United States Patent [19]

Coleman et al.

[11] Patent Number: 4,564,689
[45] Date of Patent: Jan. 14, 1986

[54] PRODUCT SEPARATION FROM ELECTROLYTE SALTS MAINTAINED IN MOLTEN STATE

[75] Inventors: James P. Coleman, Maryland Heights; Dudley E. McMackins, St. Charles, both of Mo.

[73] Assignee: Monsanto Company, St. Louis, Mo.

[21] Appl. No.: 503,982

[22] Filed: Jun. 13, 1983

[51] Int. Cl.$^4$ ............................................ C07D 307/32
[52] U.S. Cl. ..................................... 549/326; 560/241
[58] Field of Search ......................... 549/326; 560/241

[56] References Cited

U.S. PATENT DOCUMENTS

| | | | |
|---|---|---|---|
| 3,927,051 | 12/1975 | de Klein | 260/413 |
| 3,992,417 | 11/1976 | Dessau et al. | 260/343.6 |
| 4,158,741 | 6/1979 | Goi et al. | 562/599 |
| 4,175,089 | 11/1979 | Heiba et al. | 260/343.6 |
| 4,193,886 | 3/1980 | Schoenholz et al. | 252/90 |
| 4,356,317 | 10/1982 | Coleman et al. | 560/241 |
| 4,380,650 | 4/1983 | Coleman et al. | 549/326 |

OTHER PUBLICATIONS

Parshall, Catalysis in Molten Salt Media, J. Amer. Chem. Soc. 94, pp. 8716–8719, (1972).
Swain et al, J. Amer. Chem. Soc. 89, pp. 2648–2649 (1967).
Weinberg et al, Tetrahedron Letters, No. 25, pp. 2271–2274 (1971).
Michels and Ubbelohde, J. Chem. Soc. (Perkin Transactions, 1972), pp. 1878–1881.
Techniques and Methods of Organic and Organometallic Chemistry, vol. 1, Edited by Donald B. Denney (Marcel Dekker, New York and London, 1969) pp. 51, 91, 149.

Primary Examiner—Norma S. Milestone
Attorney, Agent, or Firm—Joseph D. Kennedy; James W. Williams, Jr.

[57] ABSTRACT

In processes for reacting acetic acid with butadiene in solvent to prepare acetoxyhexenoic acid and γ-vinyl-γ-butyrolactone, involving electrolytic regeneration of a metal ion oxidant such as trivalent manganese, the product separation is facilitated by using low melting electrolyte salts and separating product from salts maintained in a molten state.

7 Claims, No Drawings

PRODUCT SEPARATION FROM ELECTROLYTE SALTS MAINTAINED IN MOLTEN STATE

The present invention relates to a method of preparing γ-vinyl-γ-butyrolactone in liquid media, and isolating the γ-vinyl-γ-butyrolactone product therefrom. In particular, it concerns the separation of γ-vinyl-γ-butyrolactone product from liquid salt electrolytes and return of the salt electrolytes to the preparative process for the lactone.

BACKGROUND OF THE INVENTION

A commonly assigned U.S. Pat. No. 4,356,317 of Coleman, Hallcher and McMackins, issued Oct. 26, 1982 describes a procedure to react butadiene and acetic acid with metal ion oxidant to prepare acetoxyhexenoic acids. Commonly assigned U.S. Pat. No. 4,380,650 of Coleman, Hallcher and McMackins, issued Apr. 19, 1983, describes a procedure for converting acetoxyhexenoic acids to γ-vinyl-γ-butyrolactone. A. U.S. Pat. No. 4,175,089 describes a procedure for reacting olefins and acetic acid with metal ion oxidant to produce lactones. The prior procedures are generally conducted in solvents, e.g., in acetic acid, and separation of the product generally involves extraction procedures utilizing two immiscible solvents, such as diethyl ether and water. Particular separation procedures for γ-butyrolactones are described in U.S. Pat. No. 3,992,417. Such procedures may employ a solvent for the lactone along with a non-solvent for the lactone which is, however, a solvent for the salts formed from the metal ion oxidant. The solvent for the metal salts then is removed prior to return of regenerated metal ion oxidant to the reaction zone. Similarly, removal of the lactone solvent from product will be necessary, and its removal may also be required before recycle of unreacted olefin. When water is the solvent for metal salts, considerable care in its removal is required to avoid contamination of the reaction medium.

The commonly assigned U.S. Pat. No. 4,356,317 referenced above is primarily concerned with production of acetoxyhexenoic acids rather than lactones. It happens that reaction rates and other factors are better under conditions producing acetoxyhexenoic acids. However, it has been found that γ-vinyl-γ-butyrolactone is more stable under preparation and distillation conditions than 6-acetoxy-4-hexenoic acid and 4-acetoxy-5-hexenoic acid, and therefore is a better compound for isolation purposes. Procedures for preparing acetoxyhexenoic acids and converting the acids to γ-vinyl-γ-butyrolactone are described and claimed in a simultaneously filed, commonly assigned copending application of Coleman et al, Ser. No. 503,979, now U.S. Pat. No. 4,526,990. The procedures of that application can be employed in the present invention to provide lactone-containing reaction mixtures for product separation.

SUMMARY OF THE INVENTION

The present invention involves removing reaction solvent and product, particularly lactone product from the metal oxides and electrolyte salts from a reaction mixture, which are maintained in a fluid state even in substantial absence of solvent. The salts are such as to remain molten at the temperature at which the solvent and product are removed from the reaction mixture. The product solution from the electrolysis cell can be taken to a conventional stripping device, and solvent and product can be evaporated and taken overhead to a distillation column for separation, while the salt residue remains molten and can be pumped to a mix tank for recombination with solvent for return to the reaction zone. The salts are chosen so as to have requisite melting characteristics, as in a particular example including lithium acetate along with potassium or other alkali metal acetates in order to lower the melting point of the latter. Inorganic and organic salts can both be used if possessed of suitable melting characteristics, although many inorganic salts are too high melting to be of interest. The product separations involved will usually be accomplished at temperatures no greater than about 175° C., so it is desirable to employ salt compositions which are substantially liquid at that temperature, or at even lower temperatures if lower operating temperatures are selected. In any event, the salt composition should be in a substantially liquid state at the chosen temperature, which preferably may be around 150°–155° C. or not over about 160° C. In addition, if distillation of product is effected at 150° C., it may be convenient to employ salts which are liquid at somewhat lower temperatures, such as around 100° C., or so, to allow for some cooling without solidification in material transfer procedures, such as in pumping the salts to a solvent mix tank, or back to a reaction vessel. Of course, if necessary, heating means can be employed to maintain a suitable temperature during such operations. The invention also concerns lactone-containing product mixtures containing low melting salts, including lithium salts.

DETAILED DISCLOSURE

The present invention is concerned with effecting product separations, but the processes producing the products, and the materials employed therein, are necessarily related to the product separations.

Certain processes involving reactions of butadiene and acetic acid can be used to prepare lactones or acetoxyhexenoic acids, or to prepare acetoxyhexenoic acids which are then converted to a lactone. To achieve product separations as proposed herein, it is necessary to employ low melting salts in the preparative processes. The description herein will include description of several processes producing product-containing reaction mixtures which can be treated for product recovery in accord with the present invention. The acetoxyhexenoic acid preparation processes described are included as providing an acetoxyacid product for separation, as well as part of a described process for preparing acetoxyhexenoic acids for in situ conversion to γ-vinyl-γ-butyrolactone.

As stated in the above-referenced U.S. Pat. No. 4,356,317, metal oxidants other than manganese can be used, e.g., vanadium or cerium, for the reaction of butadiene and acetic acid. Also acids other than acetic can be used to produce acyloxyhexenoic acids which can be de-acylated to lactones. However, the preferred manganese and acetic acid will be used herein for exemplifification.

The processes producing acetoxyhexenoic acids and γ-vinyl-γ-butyrolactone involve reaction of butadiene and acetic acid, generally at somewhat elevated temperature, in the presence of a metal oxidant, particularly manganese ion in a valence higher than its lower positive valence, and preferably in acetic acid solution with electrolytic regeneration of the higher manganese valence. The processes are directed toward production of acetoxyacids if substantial amounts of acetic anhydride are included in the reaction mixture or other provisions are taken to provide substantially anhydrous conditions. The reaction medium is provided with electrolyte salts for the electrolytic regeneration, which salts have low melting characteristics as described herein.

The referred to U.S. Pat. No. 4,356,317 concerns a process in which butadiene and acetic acid are reacted in the presence of a metal salt oxidant, usually trivalent manganese, to produce acetoxyhexenoic acids. Acetic anhydride is also present with the effect of enhancing the reaction rate and selectivity of the process to acetoxyhexenoic acids. The acetoxyhexenoic acids produced are 6-acetoxy-4-hexenoic acid and 4-acetoxy-5-hexenoic acid. The process is conducted on a continuous basis with electrolytic regeneration of the trivalent manganese. The reaction stream can be cycled from a reactor through the anode chamber of a divided electrolysis cell to achieve such regeneration. Cupric ion is also preferably used in the process described in said application, and it too is regenerated electrolytically or by reaction with regenerated manganese III.

During a process for producing acetoxyhexenoic acids, the reaction mixture will contain acetic acid, acetic anhydride and manganese and copper ions. The manganese will generally be in the divalent or trivalent state, and the copper in the divalent or monovalent state. In a continuous process in which the reaction mixture is cycled through an anode chamber for oxidation of metal salts, a substantial amount of the manganese will be in trivalent state, and copper in divalent state, after the mixture has been subjected to such oxidation. For that part of the reaction mixture which has been permitted to react extensively, as in a reaction chamber immediately before being cycled to the anode chamber of an electrolysis cell, the supply of trivalent manganese and divalent copper may be nearly exhausted, as the metal ions are reduced in reactions oxidizing other components of the reaction mixture. The reaction mixture will also contain butadiene, but the amount may be relatively low after extensive reaction before recycle.

It is desirable to convert the acetoxyhexenoic acids to $\gamma$-vinyl-$\gamma$-butyrolactone for isolation purposes. It has been found that monovalent copper effectively catalyzes the conversion of acetoxyhexenoic acids to $\gamma$-vinyl-$\gamma$-butyrolactone, and that such conversion can occur upon heating the acetoxyhexenoic acids and monovalent copper in the presence of manganese and other components of a reaction mixture containing acetoxyhexenoic acids. However, the copper must be monovalent to be effective. Since monovalent copper cannot exist to a significant extent in the presence of trivalent manganese, it is necessary that manganese present be in the divalent or lower valence state. Of course, nominal amounts of trivalent manganese can be tolerated, if insufficient to oxidize substantially all of the cuprous ion present. Thus, an effective process involves the use of cuprous ion and heat to convert acetoxyhexenoic acids to $\gamma$-vinyl-$\gamma$-butyrolactone, and particularly such use in the presence of manganese. The processes involving conversion to lactone, as described herein are further described in the aforesaid simultaneously filed copending application Ser. No. 503,979, now U.S. Pat. No. 4,526,990.

The conversion to lactone can be effected by heating acetoxyhexenoic acids, preferably in a solvent, with cuprous ion. The cuprous ion can be supplied in the form of cuprous acetate, cuprous chloride, cuprous oxide, etc. Also, copper can be provided in various forms and converted in situ to the cuprous form. Thus, various cupric salts can be reduced to cuprous salts. For example, a solution of cupric acetate containing acetoxyhexenoic acids can be subject to reduction at the cathode of an electrolysis cell, or be contacted with hydrogen gas, to convert the cupric acetate to cuprous acetate, and heating will then readily convert the acetoxyhexenoic acids to $\gamma$-vinyl-$\gamma$-butyrolactone. A wide range of temperatures will be operable for the conversion, such as from about 60° C., to about 200° C., but to obtain desirable reaction rates without unnecessarily high temperatures, it may be advantageous to use temperatures in the range of about 100° C., to about 180° C., or so. The amount of cuprous ion used can vary widely, but will often be in the range of about 2% to about 40% by weight of the acetoxyhexenoic acids. Similar amounts of platinum can be used, and ordinarily in zero valent state. In the event the acetoxyhexenoic acids are produced in a process using manganese and copper ions, it will generally be appropriate to use the copper in the quantity present in the reaction mixture, using means to reduce it to the cuprous state if necessary.

The melting points of salts can be used as a guide in selection of salts for use herein. However, because of the usual presence of both metal oxidant and electrolyte salts in the present process, melting point-lowering effects of mixtures are involved, and a particular mixture with suitably low melting characteristics can be employed even if some components have melting points which are higher than chosen operating temperatures. If desired, eutectic mixtures of salts can be employed, but other salt mixtures of sufficiently low melting characteristics can be employed.

As indicated above, lithium salts are useful in lowering the melting point of alkali metal salt mixtures, particularly alkali metal acetates. In the reactions exemplified herein, a metal oxidant is employed, preferably a manganese compound, although cesium and vanadium compounds can also be used. Also, it is generally preferred to use copper compounds in conjunction with the manganese compound. Thus the salt compositions in the present process usually include manganese (or other metal oxidant) and copper salts along with electrolyte salts. Alkali-metal salts are convenient for use as electrolyte to improve conductivity, although other supporting electrolytes can be used. Manganese and copper salts contribute to conductivity, but it is desirable to have other electrolyte salts present.

Since the reactions exemplified herein involve reactions of acetic acid (directly or indirectly), it is convenient to use acetate salts as electrolytes in the process. An excess of acetic acid can also be conveniently used as solvent. The use of acetate salts avoids possible complication of separation or other procedures by unnecessary presence of extraneous ions. Potassium or sodium acetates can be used suitably in conjunction with lithium acetates, and such combinations can be employed with the usual ranges of manganese and copper salts. The manganese and copper compounds can also be considered as acetates in the usual acetic acid media, regardless of the form in which added to the reaction mixture.

With acetate salts, lithium is particularly useful as a cation to lower melting points, but ammonium acetates can also be used, including that of the ammonium ion, as well as mono-, di- or trisubstituted or quaternary ammonium ions. Particular salts of cations other than lithium will have suitably low melting points, such as particular salts of carboxylic acids, such as of medium to higher molecular weight carboxylic acids, or, with some cations, the halide or thiocyanate salts can suitably be employed. In the case of ammonium, substituted ammonium and quaternary ammonium cations, a number of anions provide salts of suitably low melting point.

In the separation procedures herein, a salt residue will be obtained which is primarly composed of the metal oxidant and electrolyte salts. However, an absolutely complete separation of product will not ordinarily be obtained and the salt residue will have some residual product and solvent present, such as small, minor amounts of γ-vinyl-γ-butyrolactone or acetoxyhexenoic acids, and even very small amounts of acetic acid. Such materials, even though small in amount, will have some tendency to liquefy the salts at temperatures lower than would be required otherwise, and this can be taken into consideration when selecting salts for suitable properties. During and prior to completion of distillation, of course, the salts will necessarily be accompanied by the product or other material being distilled, which will have some tendency toward liquefying the salt composition. It is likely that even some small amount of acetic acid is still present in the salts, in a form analogous to water of hydration, after the bulk of the desired product has been distilled. Even such small amounts of acetic acid are apt to have some effect in lowering the melting point of the salts.

In carrying out the present invention, reaction conditions in general can be employed which are suitable for preparation of acetoxyhexenoic acids or γ-vinyl-γ-butyrolactone, but with use of salts in the reaction mixture which have low melting point characteristics as described herein. Thus, manganese and copper compounds can be utilized in the usual manner, along with an electrolyte salt such as potassium acetate. A sufficiently low melting point can then be assured by inclusion of lithium acetate, either as replacement for all or part of the usual amount of potassium acetate, or in addition thereto. Lithium acetate can be used as the sole electrolyte salt if desired. However, cost or other considerations may make it desirable to use lithium acetate along with potassium acetate, with potassium being present on a mol basis in up to a 7:1 ratio to lithium, preferably from about 1:1 up to about 5:1 mol ratio of potassium to lithium. Similar proportions can be used with mixtures of lithium and sodium acetates, although sodium acetate itself is somewhat higher in melting point than potassium acetate. The actual melting characteristics of compositions are influenced by type of composition, such as solid solution, congruent compound, and whether a eutectic composition is formed, and in the present instance by the presence of minor amounts of manganese and copper salts along with those of other cations, such as lithium and other alkali metals. Mixtures of several electrolyte salts can also be used, e.g. mixtures of sodium, potassium and lithium acetates, and in some cases having a third component may contribute to lower melting characteristics. Various ammonium ions may be used, with ammonium acetate itself having a fairly low melting point. Quaternary ammonium salts for the most part have relatively low melting points, and in particular, quaternary ammonium salts, such as tetrabutyl ammonium salts, or salts of other tetraalkyl ammoiun ions with alkyl groups of at least 4 carbon atoms, tend to have low melting points, with this being true for the chloride, bromide iodide, acetate, etc. salts.

Quaternary ammonium salts of various carboxylic acids can be used. Suitable low melting electrolyte salts, can, for example, be composed of mixtures of low melting quaternary ammonium salts, particularly those with substituents on the nitrogen atom having at least four carbon atoms, with one or more alkali metal salts. For example, such quaternary ammonium salts, particularly acetate salts, may be used in admixture with potassium acetate; if desired, lithium acetate can also be included to obtain the effects of both the lithium and quaternary ammonium salts on the melting characteristics. It will be recognized that there will be considerable variation in the melting characteristics of various salt compositions, but one can readily determine whether particular mixtures have suitable melting characteristics for particular operating conditions.

In addition to melting characteristics, the electrolyte salt selected should have suitable properties as an electrolyte and should not unduly interfere with the desired reactions. Salts with anions such as sulfonates, e.g. toluenesulfonate, or phosphonates are not likely to interfere, and the quaternary ammonium salts with such anions, particularly with tetrabutylammonium or other quaternary ammonium cations described above, are likely to have low melting characteristics. Quaternary ammonium benzoate salts also tend to be low melting, particularly tetrahexylammonium benzoate which is a liquid at room temperature and is unlikely to interfere in electrolysis by discharge at the electrodes. Acetate salts are particularly suitable as acetates and acetic acid are involved in the desired reactions, and acetates have been demonstrated to be useful supporting electrolytes to carry the electric current. However, salts with other anions give good conductivity and carry electric current, and can be employed herein, although consideration should be given to effectiveness compared to the acetate, and potential interference in the chemical reactions or by unwanted discharge at the anode. Also, it will be desirable to utilize electrolyte salts which can be dissolved in wanted quantities in the electrolysis medium.

The supporting electrolyte salt is employed in the reaction to improve conductivity for electrolysis, and any concentrations achieving this are suitable for use. The manganese and copper salts which are present provide some conductivity but it is not generally sufficient for operation at reasonably high currents for desirable production rates. Suitable concentrations will generally be in the range of about 0.5 to about 3 moles of electrolyte salt per liter of reaction medium and often from about 1 to about 2 moles on such basis, and such ranges are suitable for various alkali metal acetates, or for other salts described herein, provided that solubility limits for particular salts are not exceeded. Amounts of salt which are not dissolved, may have little effect.

A process for preparation of acetoxyhexenoic acids and conversion to lactone can be visualized as follows. Butadiene and solvent electrolyte and other components are added to a recycle line and enter a first reactor for reaction at elevated temperature. The discharge from the reactor comprising some acetoxyhexenoic acids, reactants, and substantial concentrations of manganous ion, flows through a line to a first electrolysis cell for oxidation where manganous ion is oxidized to manganic ion. The discharge from the electrolysis cell flows through a recycle line to the reactor. A side stream is taken off reactor effluent which can go to a holding and heating vessel for further reaction in order to reduce any remaining trivalent manganese to divalent manganese. The mixture then flows through the cathode chamber of a second electrolysis cell to reduce cupric ion to cuprous ion, and then to a second reactor for heating to convert the acetoxyhexenoic acids to γ-vinyl-γ-butyrolactone. From the second reactor it proceeds to the first electrolysis cell for oxidation of the manganous ion and thence to the first reactor.

For product separation, part of the reaction stream can be permitted to flow from the second reactor through a side stream to a separation zone. There, the acetoxyhexenoic acids and γ-vinyl-γ-butyrolactone can be separated from the other components, and discharged, while other components are returned to the reaction system.

A suitable product separation can be visualized as follows. A product solution from an electrolysis cell or reactor is conducted to a stripping device wherein it is heated and solvent and product, e.g. γ-vinyl-γ-butyrolactone, are evaporated and taken overhead to a distillation column. The salt residue in the stripping device is molten and flows in liquid state from the stripping device, and can be recycled to the electrolysis cell or reactor. In the distillation column the solvent and product, e.g. acetic acid and γ-vinyl-γ-butyrolactone, are separated, and the solvent taken overhead can be recycled to the electrolysis or reactor. If desired, the solvent from the distillation column and salts from the stripping device can be recombined in a mix tank prior to recycle to the cell or reactor.

In the product separations herein, it will generally be advantageous to distill product in lactone form, as γ-vinyl-γ-butyrolactone can be more readily distilled than can its related acetoxyhexenoic acids. The γ-vinyl-γ-butyrolactone can be distilled at approximately 150° C. at 90 mm, Hq., while a mixture of 4-acetoxy-5-hexenoic and 6-acetoxy-4-hexenoic acids require a pressure less than about 0.1 mm Hg for distillation at 130°–150° C. Thus the acetoxyhexenoic acids can be separated by distillation in accord with the present invention, although practical considerations weigh against such procedure for large scale use. An organic solvent, e.g. a hydrocarbon solvent, can be used to extract acetoxyhexenoic acids from molten salts, with some handling advantage in having the salts in molten state.

The present product separations can be effected with processes with usual concentrations of materials for the acetoxyhexenoic acid preparation, for example, with acetic acid and acetic anhydride as a solvent system with a range of about 0.2 to about 0.8 mole acetic anhydride per mole acetic acid, manganese ion in the range of about 10 to 300 millimoles per liter, with electrolytic regeneration to provide about 10 to about 50 millimoles of the manganese in the trivalent state, butadiene in the range of about 0.05 to 0.3 moles per liter, and copper in about 5 to 150 millimoles. The process might be conducted in a temperature range of about 80° to about 120° C. Additional reactants can be added to maintain such concentrations, and the product take-off stream can be adjusted to have a desired product concentration in the reaction mixture. Higher temperatures can be used, such as up to 250° C. Of course, supporting electrolyte salts, as described herein, will also be present.

If it is desired to produce the lactone directly, the acetic anhydride will be omitted, and conditions in general as in the above referred to U.S. Pat. No. 4,175,089 can be used.

In part, the present application is concerned with a process involving the conversion of acyloxyhexenoic acids to γ-vinyl-γ-butyrolactone, and particularly such conversion in the presence of reactants and other components of the reaction mixture in which the acyloxyhexenoic acids were produced. While various means can be used, any method effective for the conversion is suitable. Heating to elevated temperatures is a simple method of effecting the conversion. While this method is usually relatively slow, it may be useful under some circumstances. Temperatures in the range of 100° to 180° C. or so can be used, and it may at times be desirable to use even higher temperatures. The use of high temperatures may be more effective in some cases than others, for example, depending upon the presence and concentration of other components of a reaction mixture containing acetoxyhexenoic acids.

EXAMPLE 1

A reaction and electrolysis system was utilized which had an electrolysis cell with separate anolyte and catholyte circulation loops, both equipped with reservoirs. The anolyte loop also had a secondary reservoir, equipped with electrodes, and a hold tank and means for cycling material through the secondary reservoir, as well as for transferring material from the primary anolyte loop to the secondary anolyte reservoir, and from the secondary anolyte reservoir back to a hold tank and thence to the primary anolyte reservoir. The system allowed production of acetoxyhexenoic acids in the primary system, followed by conversion to γ-vinyl-γ-butyrolactone in the secondary system. By utilizing two anolyte charges, the processes can be carried out simultaneously.

An anolyte solution consisting of:

| | |
|---|---|
| Manganese (II) acetate, tetrahydrate | 150 g. |
| Copper (II) acetatemonohydrate | 43 g. |
| Potassium acetate | 428 g. |
| Lithium acetate dihydrate | 54 g. |
| Acetic acid | 1400 ml. |
| Acetic anhydride | 1050 ml. | and a catholyte solution consisting of:

| | |
|---|---|
| Potassium acetate | 300 g, |
| Acetic acid | 2410 ml. |
| Acetic anhydride | 90 ml. | were charged to their respective primary reservoirs and maintained at about 100° C. The anolyte was kept saturated with 1,3-butadiene.

The system was electrolyzed for 10 hr at 5 amps current after which time 200 g of potassium acetate was added and the anolyte was transferred to the secondary reservoir. A new charge of the same anolyte solution was charged to the primary reservoir and electrolyzed as above with addition of butadiene. Concurrently, the anolyte solution in the secondary reservoir was subjected to 1 hr of electrolysis at 1.5 amps at 100°–130° C., held for 3 hr at reflux (130°–135° C.) to convert the acetoxyacids product to lactone, then allowed to cool to 100° C. The original anolyte was then returned to the primary reservoir via the hold tank while the contents of the primary reservoir were transferred to the secondary reservoir. The process was thus repeated until each batch of anolyte had experienced in order 2 cycles of 50 Amp. hr. electrolysis in the primary reservoir followed by the above described 1.5 amp. hr electrolysis and reflux treatment in the secondary reservoir.

During the process the concentration of acetoxyhexenoic acids in each cycle rose to slightly over 4.5% by weight, and dropped to less than 1% after the first conversion to lactone, and was slightly over 1% by weight after conversion to lactone in the second cycle. The current efficiency to product at the time of a total product concentration, calculated as acetoxyhexenoic acid, of 8.5%, was better than 80%. Thus a lactone concentration circa 7.5% was obtained with good current efficiency.

A Pope Scientific jacketed 2 inch diameter wiped film molecular still was modified and attached at its lower outlet to a separation distillation column below the midpoint of the column. The wiped surfaces were maintained at approximately 155°–160° C. by circulating heated oil through the jacket. The vapor outlet from the still was heated to prevent condensation before entering the column. The column was 2.5 cm internal diameter by 80 cm long and was packed with 3/16" glass helices. A 3 cm length of the bottom of the column was maintained at 135°–140° C. to serve as a reboiler. The center 55 cm of length of column was maintained at about 100° C. by circulation of heated fluid through a jacket surrounding this section. No heat was applied to the top 22 cm length of the column. Vapor exiting the top of the column was condensed at about 20° C. The entire system was maintained at about 80 mm Hg pressure via a vacuum pump.

A 2024 g. portion of the above product anolyte solution containing 92.8 g of γ-vinyl-γ-butyrolactone was fed over about 4.6 hr into the top of the wiped film still. The residual salt heel remained fluid and was collected separately from an outlet at the bottom of the wiped film still after flowing down the walls of the still. 102.5 grams of liquid was collected from the bottom of the distillation column and analysis showed it contained 75.2 g of γ-vinyl-γ-butyrolactone. The salt residue was molten liquid at 150°–155° C. or so, but tends to solidify at somewhat lower temperature, 140° C. or so.

About 1450 g of liquid was collected from the top of the column and analysis showed it to contain 7.4 g. of γ-vinyl-γ-butyrolactone.

Further description of procedures for preparing acetoxyhexenoic acids and converting such acids to γ-vinyl-γ-butyrolactone is found in the aforesaid simultaneously filed patent application of Coleman et al Ser. No. 503,979, now U.S. Pat. No. 4,526,990, the disclosure of which is incorporated herein by reference.

EXAMPLE 2

The product separation of Example 1 was repeated, except that the feed solution consisted of:

| | |
|---|---|
| Manganese (II) acetate tetrahydrate | 15 g. |
| Copper (II) acetate monohydrate | 4.2 g. |
| Potassium acetate | 31.5 g. |
| Lithium acetate dihydrate | 6.3 g. |
| Acetic acid | 165 ml |
| Acetic anhydride | 105 ml |
| α-vinyl-α-butyrolactone | 26.8 g. |
| Acetoxyhexenoic acids | 5.0 g. | and was fed over about 0.8 hr. Analytical results are as follows:

Still bottom liquid: 28.5 g. total wt. 24.2 g. γ-vinyl-γ-butyrolactone

Still top condensate: 272 g. total wt. Contains no γ-vinyl-γ-butyrolactone

Salt heel contains: 3.8 g γ-vinyl-γ-butyrolactone 2.7 g. Acetoxyhexenoic acids

EXAMPLE 3

A 100 ml 3-neck flask was equipped with an addition funnel, mechanical stirrer and a short-path still head with receiver and vacuum take-off. The flask was immersed in an oil bath maintained at 150° C. A solution of electrolyte salts and electrolysis products was made up and added through the addition funnel over 35 minutes while maintaining 90 mm Hg of pressure.

| Solution | |
|---|---|
| $Mn(OAc)_2 \cdot 4H_2O$ | 5 g |
| $LiOAc \cdot 2H_2O$ | 1.9 g |
| KOAc | 10.5 g |
| $Cu(OAc)_2 \cdot H_2O$ | 1.4 g |
| HOAc | 55 ml |
| $Ac_2O$ | 35 ml |
| α-vinyl-α-butyrolactone | 8.02 g |
| 4-Acetoxy-5-hexenoic acid + | |

Condensate was taken off via the still head leaving a molten salt mixture in the stirred flask. Analysis of the condensate showed that essentially all of the HOAc+$Ac_2O$ had distilled out along with 7.63 g of γ-vinyl-γ-butyrolactone. Analysis of the residual salt cake showed it to contain 0.22 of the lactone and 0.82 g of the isomeric acetoxyacids.

EXAMPLE 4

A 2" Jacketed Pope wiped film molecular still was modified with an external condenser and 160° C. heating oil was circulated through the jacket and the existing condenser. A solution of electrolyte salts and electrolysis products was added through a dropping funnel over 45 minutes. Pressure of 90 mm Hg was maintained.

Solution 15 g Mn $(OAc)_2.4H_2O$
28 g KOAc
9.4 g $LiOAc.2H_2O$
4.2 g $Cu(OAc)_2.H_2O$
100 ml $Ac_2O$
170 ml HOAc
24.0 g γ-vinyl-γ-butyrolactone
2.5 g 4-Acetoxy-5-hexenoic acid + 6-Acetoxy-4-hexenoic acid.

Low boilers were condensed in the external condenser and the molten salt residue flowed down the wiped surface of the still and was collected. Analysis of the condensate showed that essentially all of the HOAc and $Ac_2O$ had distilled out along with 21.3 g of γ-vinyl-γ-butyrolactone. Analysis of the residual salt cake showed it to contain 2.5 g of the lactone and 4.2 g of the isomeric acetoxyacids.

What we claim is:

1. A process for preparing γ-vinyl-γ-butyrolactone in which butadiene and acetic acid are reacted in the presence of metal ion oxidants with electrolytic regeneration of such oxidants during the reaction, and the reaction is carried out in liquid solvent medium containing salts comprising manganese salts employed as oxidants and electrolyte salts at temperatures in the range of 100° C. to 180° C. and separating γ-vinyl-γ-butyrolactone by distillation at a temperature sufficiently high to leave salt residue in a molten state and in the range of about 140° to about 175° C., and the salts are recycled to the reaction, and in which the salt composition present is in liquid state at a temperature in the range of about 140° C. to about 175° C.

2. The process of claim 1 in which the product and solvent are distilled from the reaction mixture at a temperature no greater than about 160° C., leaving a molten salt residue.

3. The process of claim 2 in which the salts contain lithium salts to lower the melting point thereof.

4. The process of claim 2 in which the salts comprise alkali metal acetates, including lithium acetate, along with manganese and copper salts.

5. The process of claim 1 in which butadiene and acetic acid are reacted in the presence of acetic anhydride to produce acetoxyhexenoic acids and the reaction mixture is subsequently heated to convert the acetoxyhexenoic acids to γ-vinyl-γ-butyrolactone, and the lactone is distilled from the molten salts at a temperature no greater than about 160° C.

6. A process of preparing and recovering γ-vinyl-γ-butyrolactone which comprises reacting butadiene, acetic anhydride, acetic acid and trivalent manganese as a metal ion oxidant in a reaction medium comprising acetic acid as solvent with acetic anhydride in the range of about 0.2 to about 0.8 mole per mole acetic acid, manganese in the range of about 10 to about 300 millimoles per liter, butadiene in the range of about 0.05 to about 0.3 mole per liter, copper in the range of about 0.05 to about 0.3 moles per liter, copper in the range of about 5 to about 150 millimoles per liter, and alkali metal acetates in the range of about 0.5 to about 3 moles per liter, with a portion of the alkali-metal being lithium, with trivalent manganese being regenerated by electrolysis during the course of the reaction, and in a subsequent stage converting acetoxyhexenoic acids to γ-vinyl-γ-butyrolactone in a heating step, at temperatures of about 60° to about 200° C. in the presence of cuprous ion and separating the γ-vinyl-γ-butyrolactone from the reaction mixture by distillation at a temperature sufficiently high to leave salt residue in a molten state and in the range of about 140° C. to about 175° C. and in which the salt composition present is in liquid state at a temperature in the range of about 140° C. to about 175° C.

7. The process of claim 6 in which lithium and potassium acetates are present in a ratio between about 1:1 and about 1:7 lithium to potassium on a mole basis.